(12) United States Patent
Yu

(10) Patent No.: US 6,271,250 B1
(45) Date of Patent: Aug. 7, 2001

(54) METAL GLYCIDIDAAGOLC, AND PREPARATION AND USES THEREOF

(75) Inventor: Ruihong Yu, Guangdon (CN)

(73) Assignee: S&H Pharm Technology Co., Ltd, Guangdong (CN)

( * ) Notice: Subject to any disclaimer, the term of this patent is extended or adjusted under 35 U.S.C. 154(b) by 0 days.

(21) Appl. No.: 09/544,130

(22) Filed: Apr. 6, 2000

(30) Foreign Application Priority Data

Apr. 8, 1999 (CN) .................................................. 99116128

(51) Int. Cl.[7] .................... C07D 403/12; A61K 31/4155; A61P 31/00

(52) U.S. Cl. ........................................ 514/397; 548/313.7

(58) Field of Search .......................... 548/313.7; 514/397

(56) References Cited

PUBLICATIONS

Yang, et. al, 1987, Fushe Yanjiu Yu Fushe Gongyi Xuebao, 5(1).*

Zheng, et. al., 1995, Fushe Yanjiu Yu Fushe Gongyi Xuebao, 13(4), 213–8.*

* cited by examiner

*Primary Examiner*—Deborah C. Lambkin
*Assistant Examiner*—Andrea M. D'Souza
(74) *Attorney, Agent, or Firm*—Schwegman, Lundberg, Woessner & Kluth, P.A.

(57) ABSTRACT

A compound having formula (I):

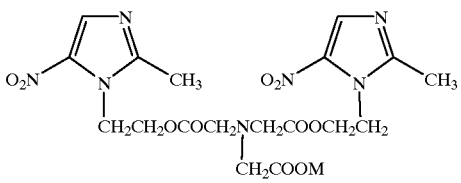

wherein M is a metal ion or a chelate thereof. The compound of the present invention is useful as sensitivity enhancers for chemotheraphy and radiotheraphy.

8 Claims, No Drawings

METAL GLYCIDIDAAGOLC, AND PREPARATION AND USES THEREOF

The present invention relates to nitroimidazole compounds, particularly a Metal Glycididaagolc, which is useful as sensitivity enhancers for chemotheraphy and radiotheraphy.

A variety of factors contribute to the efficiency of radiotheraphy and chemotheraphy. A major one of them is a fraction (10–50%) of anaerobic cells present in tumors, whose tolerance toward radiation or chemothrapeutant is 2.5–4 times higher than that of aerobic cells in tumors or normal cells. Thus, those anaerobic cells can not be efficiently killed at regular radiotherapeutic or chemotherapeutic dosage, and might induce tumor metastasis or relapse. Sensitivity enhancer is a chemical that can enhance the effect of radiation and chemothrapeutant to the anaerobic cells in tumors, but has much weaker effect to the aerobic normal tissue.

Zangondroff reported the enhanced radiation damage to mice by iodoacetic acid in 1954, which is the first time to demonstrate the effect of sensitivity enhancer. In the next decade, a lot of effort has been made to investigate the effect of sensitivity enhancer on cells. As a result, several compounds were screened, but the sensitivity enhancement is not always positive. In the early 1960s, Adams et al. established the method for screening sensitivity enhancers, and demonstrated that the nitroimidazole compounds have the sensitivity enhancement effect. However, insufficient sensitivity enhancement effect and serious gastrointestinal side effects resulted at the dosage that is required to be administered limited the clinical application of these compounds.

Since 1974, 2-nitroimidazole (MISO) had been investigated on clinical trials for more than ten years. The result shows that though 2-nitroimidazole has significant sensitivity enhancement effect, it has serious neurotoxicity, and therefore is not clinically applicable. After 1980s, a lot of new compounds, e.g. SR-2508, RSU-1069, Al-2123, DMM, RO-03-8799, have been synthesized through structural modification of MISO. Chinese patent No. 89102182.5 disclosed a method for preparation of an anticancer drug, namely, methyl nitroimidazoleamino acid. All the above mentioned compounds show unexpected side effects, and only a few of them are under further investigation. Thus, the anticancer sensitive enhancers are still not clinically applicable so far.

It is an object of the present invention to provide compound which is capable of enhancing the sensitivity of tumor cells to radiotheraphy and chemotheraphy, and therefore, enhance the damage of radiation and chemothrapeutant to tumor cells.

It is another object of the present invention to provide a process for preparing. a compound that is capable of enhancing the sensitivity of tumor cells to radiotheraphy and chemotheraphy, and therefore, enhance the damage of radiation and chemothrapeutant to tumor cells.

The sensitivity enhancers for radiotheraphy and chemotheraphy of the present invention, i.e. Metal Glycididaagolc, are compounds of the general formula (I):

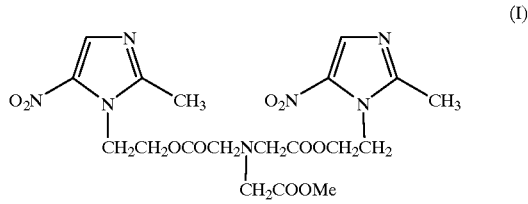

wherein Me is a monovalent metal ion, a bivalent metal ion, a multivalent metal ions or a chelate thereof, which is connected to the organic moiety by an ironic bond. Preferably, the metal ion is $Na^+$, $K^+$, $Ca^{2+}$, $Al^{3+}$, $Mg^{2+}$, $Zn^{2+}$, or $Ba^{2+}$; more preferably, the metal ion is $Na^+$, or $K^+$.

The present invention further provides a method a method for preparation of the compounds of the present invention, comprising the steps of:

a) Carrying out anhydridization reaction under heating conditions by using nitrilotriacetic acid and acetic anhydride, thereby an intermediate of nitrilotriacetic anhydride is resulted;

b) Esterifying the intermediate obtained in step a) with 5-nitroimidazole under heating to produce a glycididaagolc acid;

c) Salifing the glycididaagolc acid obtained in step (b) under heating with a salt containing a proper metal ion.

In one embodiment of the present invention, the anhydridization and esterification are carried out in N,N-dimethylformamide as the solvent at 45° C.

In a further embodiment of the present invention, the esterification is carried out at 40–45° C., and the glycididaagolc acid is obtained by adjusting pH of the reaction mixture to 3.5–4.0 with HCl, and cooling.

In another embodiment of the present invention, the salification is carried out below 70° C., and ethanol and the salt are added to control the pH of the reaction mixture in the range of 7–8, and ethanol concentration at 70–75% by weight.

In another embodiment of the present invention, the reaction of acetic anhydride and nitrilotriacetic acid is carried out in the presence of N,N-dimethylformamide at 45° C., thereby an intermediate is obtained. The mixture of the intermediate and 5-nitroimidazole is adjusted to pH 3.5–4.0 with 6N HCl, and then cooled to a temperature below 10° C. Glycididaagolc acid is obtained after cooling. The glycididaagolc acid thus obtained reacts to the salt containing a proper metal ion below 70° C. to give a metal glycididaagolc. Ethanol and metal salt are added in batches to the reaction mixture in the reaction process. The pH of the reaction mixture is controlled to 7–8. The preferred ethanol concentration for product crystallization is 70–75%.

The present invention further provides the uses of the compounds in the production of sensitivity enhancers used in radiotheraphy and chemotheraphy.

The compounds of the present invention is capable of inhibit the repairing of the damaged tumor anaerobic cells, thus is useful as sensitivity enhancers for radiotheraphy and chemotheraphy. The compound is also capable of killing anaerobic bacteria or anaerobic monads.

The compound of formula (I) may be administered in liquid or solid form on the oral, parenteral, or topical routes in all the common non-toxic, pharmaceutically accepted carriers, adjuvants and additives. The compound may also be combined with appropriate carriers to achieve delayed release of the compound. The amount to be administered is generally 300 to 1200 mg/square meter of body surface area, preferably, the amount is 800 mg/square meter of body surface area.

The compounds of the present invention are soluble in water, which is suitable to be administered as sensitivity enhancers in tumor radiotheraphy and chemotheraphy. The result of experiment shows that the compound of the present invention can significantly enhance the sensitivity of the variety of solid tumors to the radiotheraphy and chemotheraphy, and significantly reduces the noxious side effects of radiotheraphy and chemotheraphy. Since their low oil-water distribution coefficient, the compounds have lower affinity to brain tissue than other sensitivity enhancers, and therefore, have lower neurotoxicity. Further, it was demonstrated that:

1. The radiotherapeutic sensitivity enhancement effect on in vitro $V_{79}$ cells: The $LD_{50}$ of the compounds for aerobic and anaerobic cells are 35.70 mmol/l and 23.50 mmol/l, respectively. This demonstrates that the toxicity of the compounds to anaerobic cell is significantly higher than that to aerobic cell.

2. The radiotherapeutic sensitivity enhancement effect on radiated anaerobic cells: Experimental results show that the compounds have no radiotherapeutic sensitivity enhancement effect on radiated aerobic cell, the $C_{1.6}$ value is 0.48 mmol/l. The sensitivity enhancement ratio (SER value) of the compounds at a nontoxic concentration of 0.1–1.38 mmol/l is 1.26–2.32, which demonstrates that the compound selectively enhance the radiotherapeutic sensitivity on anaerobic cells.

3. Under the same experimental conditions, the radiotherapeutic sensitivity enhancement effect of the compounds is higher than that of either MISO or methyl nitroimidazole. The SER values are 1.76, 1.52, and 1.07, respectively.

4. In the therapy of lung cancer, melanoma, breast cancer and $S_{180}$, compared with the result of control experiment, the application of the compounds of the present invention significantly lowers the tumor growing rate, enhances the tumor inhibition efficiency, and prolongs the delayed time of tumor growing.

5. The effect on normal tissue and radiated normal tissue: The results of experiments on animals show that the compounds have no detectable effect on normal tissues, medullary hematopoietic cells, avoirdupois or spleen exponent.

EXAMPLE 1

Preparation of Sodium Glycididaagolc:

A mixture of nitrilotriacetic acid (A.R., 750 g), acetic anhydride (A.R., 1100 g) and N,N-dimethylformamide (1500 ml) was stirred at 45° C. for 4 hours in a four-neck reaction bottle. Then 5-nitroimidazole (950 g) was added to the reaction mixture. After additional stirring at 40–45° C. for 2 hours, a pale brown solution containing glycididaagolc acid was obtained. The mixture was eluted with 1000 ml water, pH was adjusted to 3.5–4.0 with 6 N HCl. After the mixture was incubated in a water bath below 10° C. for 1 hour, glycididaagolc acid was crystallized from the solution. The crude glycididaagolc acid was obtained by filtration and washing with distilled water until the pH is 4.0. For further purification, the crude product was dissolved in boiling 95% ethanol (the ratio of crude product to solvent is 1:15). After decoloration with active carbon and filtration, a yellow filtrate was obtained. The filtrate was placed in a refrigerator overnight, and the product crystallized from the solution. The crystalline product was obtained by filtering, washed several times with ethanol, and dried at 60° C. A purified glycididaagolc acid (about 750 g) was obtained. The purified glycididaagolc acid (750 g) and sodium bicarbonate (A.R., 100 g) were well mixed in a 3000 ml beaker, then distilled water (200 ml) and ethanol (1000 ml) were added to the mixture. The beaker is quickly placed in a water bath with a temperature below 70° C. Additional sodium bicarbonate (100 g) was added to the reaction mixture under stirring. In this process, additional ethanol was also added to the beaker to avoid the foam overflowing the beaker. After the foam disappeared, and the reaction solution became transparent, pH was measured, which was 7–8. Active carbon was added to the solution, and the reaction mixture was kept at 60–65° C. for 30 min, then filtered through paper pulp as the filter medium. A pale brown solution was obtained. After cooling to room temperature, anhydrous ethanol (about 50 ml) was added to the solution to initiate crystallization. Then the ethanol concentration of the solution was adjusted to 70–75% with ethanol. After placing the solution in a refrigerator for more than 12 hours, the product was collected by filtration. The filter cake was washed with ethanol for 2 times. A white or yellowish powder thus obtained was dried for more than 12 hours in a vacuum oven at 40° C., the product sodium glycididaagolc (about 580 g) was obtained.

The product thus obtained is a white or pale yellow crystalline powder. It is soluble in water, methanol or acetic acid, and insoluble in chloroform or cyclohexane. The pH of its aqueous solution is 6.5–7.5. Spectral properties A=0.0330c-0.0021, UV $\lambda_{max}(H_2O)/nm$: 227, 319; $IRV_{max}$ (KBr)/cm$^{-1}$: 3440, 3180, 3145, 1762, 1735, 1545, 1500, 1475, 1428, 1370, 1273, 1202, 996, 835.

EXAMPLE 2

Clinical Effect of Sodium Glycididaagolc as a Chemotherapy and Radiotheraphy Sensitivity Enhancer 96 patients suffering from lung cancer were included in this investigation, which were divided arbitrarily into a control group (conventional chemotherapy) and a test group (identical chemotherapeutic regime, sodium glycididaagolc and 80% dosage of chemotherapeutic agent). The numbers of patients in control group and that in test group are 33 and 24 for squamous cytoma, 14 and 10 for breast cancer, 3 and 12 for cellule lung cancer, respectively. All patients were diagnosed as lung cancer by clinical pathology and cast-off cell tests. They were affirmed as IIIa-IV late period according to lung cancer TNM standard of April 1986.

Conventional chemotherapy for control group is as follows: for squamous cytoma, Cope-m regime: Me-CCNU 80 mg/m$^2$ IV, d; CTX IV, d(I); VCR 1 mg/time IV, d(I); DDP 30 mg, d(1–5); MTX 30–40 mg, IV, d(1, 3, 5); for Breast cancer, Mevp16 regime: MMC 6–8 mg/m$^2$ IV, d(I); CTX 0.8 g/m$^2$ IV, d(I); VP16 0.1, IV, d(1–5); for undifferentiated cell cancer, COVAP16 regime: CTX 0.8 g/M$^2$ or Me-CCNU 80 mg/M$^2$ IV, d(I); VCR 1 mg IV, d(I); E-AIDM 40–60 mg/m$^2$ IV, d(I); VP16 0.1, IV, d(1–5). The test group was treated as the control group except that sodium glycididaagolc was administratied at a dose of 800 mg/m$^2$ body surface area in 100 ml 0.9% NaCl solution by IV, at day 0, 1, 3, 5.

Before and after therapy, the patients of both groups were examined peripheral hemogram twice a week. The therapy efficiency was classified into complete released (CR), partial released (PR), stable (S), and perish (P) according to antitumor agents evaluation standard and solid tumor identification standard promulgated by the National Ministry of Health of China.

The effect of sodium glycididaagolc on peripheral leukocyte and blood platelet was shown in table I.

TABLE I

Comparison of peripheral leukocyte and blood platelet in two groups of patients (X ± SD)

| | Leukocyte (× 10⁹/L) | | | Blood platelet (× 10⁹/L) | | |
| --- | --- | --- | --- | --- | --- | --- |
| | Before chemotherapy | After chemotherapy | P value | Before chemotherapy | After chemotherapy | P value |
| Control group | 7.50 ± 3.2 | 2.23 ± 1.1 | <0.01 | 144 ± 51 | 87 ± 33 | <0.01 |
| Test group | 8.38 ± 3.5 | 3.04 ± 0.98 | <0.01 | 151 ± 45 | 116 ± 34 | <0.01 |
| P value (between two groups) | >0.05 | <0.01 | | >0.05 | <0.01 | |

As can be seen from Table I, leukocyte and blood platelet decreased significantly after therapy for both groups, indicating side effect of chemotherapeutic agent. However, the decrease of peripheral leukocyte and blood platelet for test group was relieved significantly compared with that of control group (p<0.01). It demonstrated that sodium glycididaagolc has the effect of inhibiting the decrease of peripheral leukocyte and blood platelet.

The two groups of patients were taken X-ray films before and after therapy. The therapy efficiency of two groups was measured according to the change of tumor size from X-ray films and other clinical indications.

TABLE II

The effect of sodium glycididaagolc on the therapy of squamous cytoma

| | Total cases | CR | PR | S | P | CR + PR | P values |
| --- | --- | --- | --- | --- | --- | --- | --- |
| Control group | 33 | 0 | 9 | 16 | 8 | 9 (27.3%) | |
| Test group | 24 | 0 | 17 | 5 | 2 | 17 (70.8%) | <0.05 |

TABLE III

The effect of sodium glycididaagolc on the therapy of lung cancer

| | Total cases | CR | PR | S | P | CR + PR | P values |
| --- | --- | --- | --- | --- | --- | --- | --- |
| Control group | 14 | 0 | 2 | 5 | 7 | 2 (14.3%) | |
| Test group | 10 | 0 | 3 | 5 | 2 | 3 (30.0%) | >0.05 |

TABLE IV

The effect of sodium glycididaagolc on the therapy of undifferentiated cells cancer

| | Total cases | CR | PR | S | P | CR + PR | P values |
| --- | --- | --- | --- | --- | --- | --- | --- |
| Control group | 3 | 0 | 2 | 1 | 0 | 2 (66.7%) | |
| Test group | 12 | 1 | 7 | 4 | 0 | 8 (66.7%) | >0.05 |

Although the dosage of chemotherapeutic agent was reduced by 20%, the therapy efficiency of test group was enhanced significantly due to combined administration of sodium glycididaagolc. The efficiency (CR+PR) was 27.3% for squamous cytoma, 14.3% for breast cancer, and 66.7% for undifferentiated cell cancer in control group, whereas, the efficiency (CR+PR) was 70.8%, 30.0%, and 66.7%, respectively in test group. The effect of the compound was not significant in COAVP16 regime, as this regime itself has a very good effect in treating undifferentiated cell cancer.

What is claimed is:

1. A compound of formula (I)

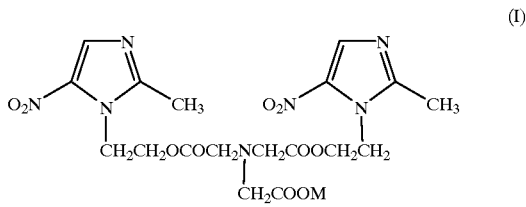

wherein M is a metal ion or a chelate thereof.

2. A compound according to claim 1, wherein M is Na⁺, K⁺, Ca²⁺, Al³⁺, Mg²⁺, Zn²⁺, or Ba²⁺.

3. A compound according to claim 1, wherein M is Na⁺, or K⁺.

4. A method for preparing the compound according to claim 1, comprising the steps of:

(a) carrying out an anhydridization reaction under heating conditions by using nitrilotriacetic acid and acetic anhydride, thereby producing the intermediate nitrilotriacetic anhydride of the following formula:

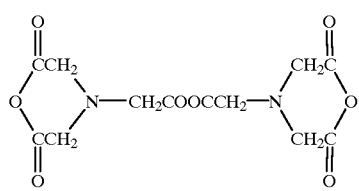

(b) esterifying the intermediate obtained in step (a) with 5-nitroimidazole under heating to produce an acid having the following formula:

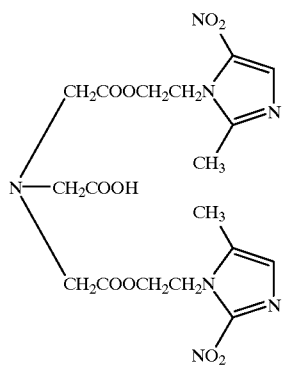

; and (c) salifing the acid obtained in step (b) under heating with a carbonate or dicarbonate containing a metal ion.

5. A method according to claim 4, wherein the anhydrization and esterification are carried out in N,N-dimethylformamide as the solvent at 45° C.

6. A method according to claim 4, wherein the esterification is carried out at 40–45° C., and the acid produced in step (b) is obtained by adjusting pH of the reaction mixture to 3.5–4.0 with HCl and cooling.

7. A method according to claim 4, wherein the salification is carried out below 70° C., and ethanol and a carbonate or dicarbonate containing a metal ion are added to control the pH of the reaction mixture in the range of 7–8, and ethanol concentration at 70–75% by weight.

8. A method for treating patients suffering from cancer, comprising administering to the patient an effective amount of the compound of claim 1.

* * * * *